United States Patent
Zhang et al.

(10) Patent No.: US 10,968,434 B2
(45) Date of Patent: Apr. 6, 2021

(54) EXOSOME ACTIVE FORMULATION FOR INHIBITING ENDOTHELIAL CELL MIGRATION, AND PREPARATION METHOD AND APPLICATION

(71) Applicant: INSTITUTE OF MICROCIRCULATION, CHINESE ACADEMY OF MEDICAL SCIENCES & PEKING UNION MEDICAL COLLEGE, Beijing (CN)

(72) Inventors: Honggang Zhang, Beijing (CN); Bingwei Li, Beijing (CN); Qiuju Zhang, Beijing (CN); Ruijuan Xiu, Beijing (CN)

(73) Assignee: INSTITUTE OF MICROCIRCULATION (OF THE CHINESE ACADEMY OF MEDICAL SCIENCES & PEKING UNION MEDICAL COLLEGE), Beijing (CN)

( * ) Notice: Subject to any disclaimer, the term of this patent is extended or adjusted under 35 U.S.C. 154(b) by 0 days.

(21) Appl. No.: 16/610,500

(22) PCT Filed: Apr. 29, 2019

(86) PCT No.: PCT/CN2019/085070
§ 371 (c)(1),
(2) Date: Nov. 2, 2019

(87) PCT Pub. No.: WO2019/210832
PCT Pub. Date: Nov. 7, 2019

(65) Prior Publication Data
US 2021/0032594 A1 Feb. 4, 2021

(30) Foreign Application Priority Data
May 3, 2018 (CN) .......................... 201810413851.7

(51) Int. Cl.
*C12N 5/071* (2010.01)
*A61K 35/44* (2015.01)

(52) U.S. Cl.
CPC .............. *C12N 5/069* (2013.01); *A61K 35/44* (2013.01); *C12N 2501/165* (2013.01); *C12N 2501/25* (2013.01); *C12N 2501/999* (2013.01)

(58) Field of Classification Search
None
See application file for complete search history.

(56) References Cited

U.S. PATENT DOCUMENTS

2016/0108368 A1 4/2016 Larocca
2020/0316134 A1* 10/2020 Ricordi ..................... A61P 3/10

FOREIGN PATENT DOCUMENTS

| CN | 107937342 A | 4/2018 |
| CN | 108753682 A | 11/2018 |
| CN | 108823144 A | 11/2018 |

OTHER PUBLICATIONS

Thery et al, Current Protocols in Cell Biology, 2006, vol. 30, Issue 1, pp. 3.22.1-3.22.29 (Year: 2006).*
Zhang, Yi-Zhe, Fan Liu, Chang-Geng Song, Xiu-Li Cao, Yu-Fei Zhang, Hai-Ning Wu, Chen-Jun Gu, Yong-Qiang Li, Qi-Jun Zheng, Min-Hua Zheng, Hua Ha "Exosomes Derived from Human Umbilical Vein Endothelial Cells Promote Neural Stem Cell Expansion While Maintain Their Sternness in Culture" Biochemical and Biophysical Research Communications, Nov. 15, 2015, vol. 495, Nr.:1, pp. 892-897, XP055648816, Communications, Nov. 15, 2015 DOI: https://dx.doi.org/10.1016/j.bbrc.2017.11.092.
Zhang, Jieyuan et al., "Exosomes released from human induced pluripotent stem cells-derived MSCs facilitate cutaneous wound healing by promoting collagen synthesis and angiogenesis", Journal of Translational Medicine,vol. 13, No. 49, Feb. 1, 2015 (Feb. 1, 2015), ISSN:1479-5876.
Wu, Quanfeng et al., "Suppression of endothelial cell migration by tumor associated macrophage-derived exosomes is reversed by epithelial ovarian cancer exosomal IncRNA", Cancer Cell International,vol. 17, No. 62, Jun. 6, 2017 (Jun. 6, 2017), ISSN:1475-2867.
Li, Xiaocong et al "Human endotherlial progenitor cells-derived exosomes accelerate cutaneous wond healing in diabetic rats by promoting endotherlia function" (Journal of Diabetes and Its Complications) vo. 30, 2016 (pp. 986-992 (Aug. 31, 2016).

* cited by examiner

Primary Examiner — Allison M Fox
(74) Attorney, Agent, or Firm — Craft Chu PLLC; Andrew W. Chu

(57) ABSTRACT

An exosome active formulation for inhibiting endothelial cell migration, and a preparation method and use thereof include the following steps: isolating primary umbilical vein endothelial cells and performing cell culture and passage; adding anisodamine to a culture medium of the subcultured endothelial cells to pretreat the endothelial cells, and then replacing the culture medium with a new endothelial cell culture medium and adding TNF-α to continue the culture of the endothelial cells; extracting exosomes from the TNF-α containing endothelial cell culture medium obtained after the endothelial cells are cultivated; and identifying the exosomes. The exosome active formulation for inhibiting endothelial cell migration prepared by the preparation method of this disclosure and its use in the antitumor drugs.

6 Claims, 3 Drawing Sheets

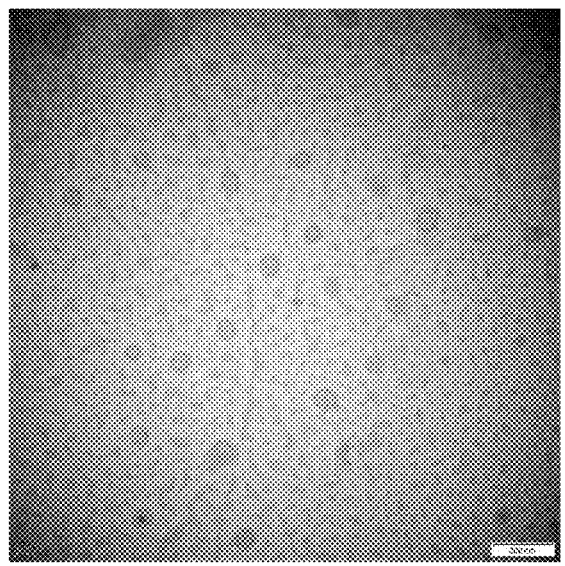 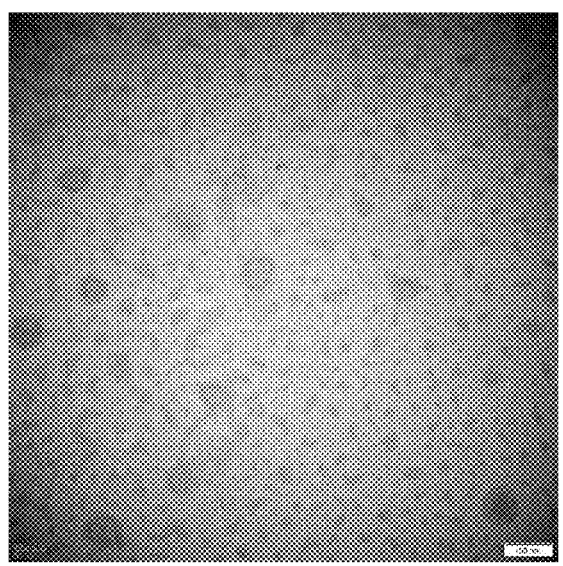
Fig. 1AFig. 1B
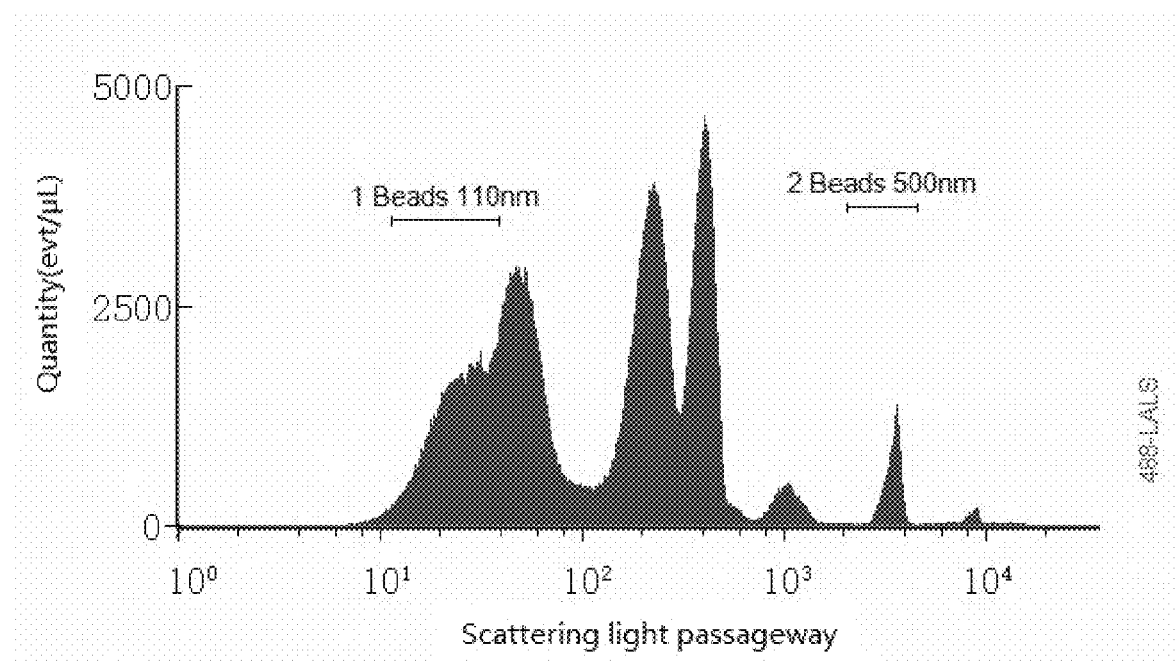
Fig. 2A

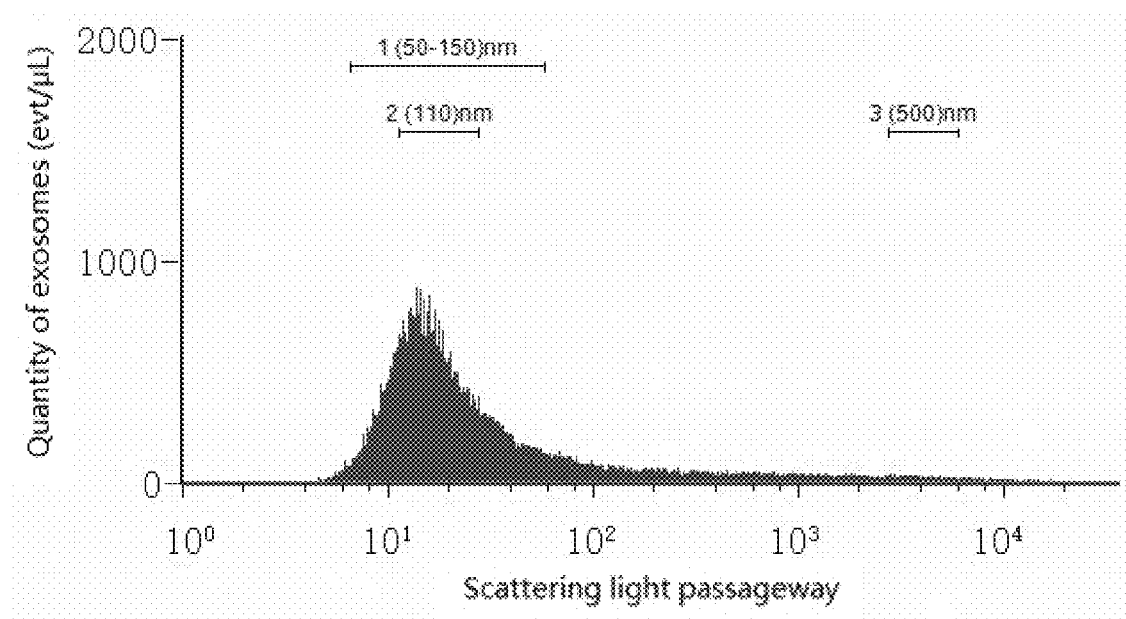
Fig. 2B
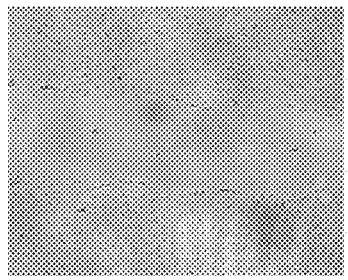
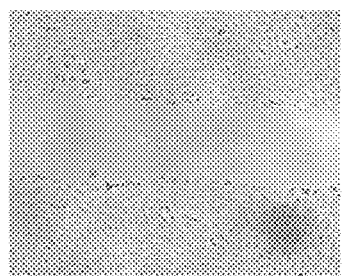
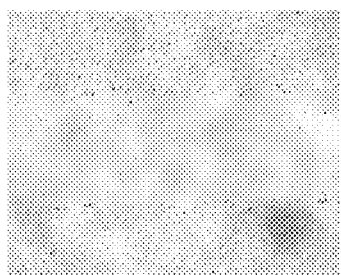
Fig. 3A Fig. 3B Fig. 3C
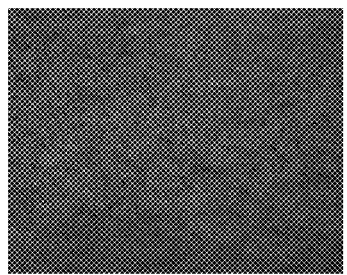
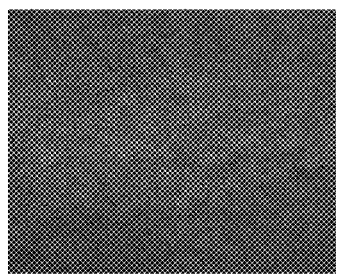
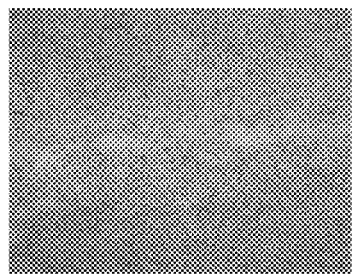
Fig. 3D Fig. 3E Fig. 3F

EXOSOME ACTIVE FORMULATION FOR INHIBITING ENDOTHELIAL CELL MIGRATION, AND PREPARATION METHOD AND APPLICATION

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

This disclosure pertains to the field of biological medicine, and particularly relates to an exosome active formulation for inhibiting endothelial cell migration, and a preparation method and application.

2. Description of Related Art Including Information Disclosed Under 37 CFR 1.97 and 37 CFR 1.98.

Cell migration is common in normal physiological activities and disease occurrence of the human body, e.g., cell migration is involved in each of the processes of embryogenesis, injury repair, immune response, cancer metastasis, etc. Angiogenesis plays an important role in the generation and development of tumors. The migration of vascular endothelial cells is one of the key steps in angiogenesis. The occurrence of tumors is accompanied by the formation of blood vessels to provide nutrients. The study on the inhibition of vascular endothelial cell migration is also important for tumor therapy. Currently, the anti-tumor angiogenesis therapy targeting vascular endothelial production factors causes various forms of adverse reactions and resistance, and the scientists are looking for new alternative pathways in this aspect.

With the deepening of research on cellar exosomes, the exosomal drug formulations increasingly become a hotspot in research on the treatment of diseases. An exosome is a transportation vesicle that is secreted and released into the extracellular environment by a living cell, and has a size of 60-100 nm. The exosome can deliver chemical drugs, proteins as well as peptide ligands, gene drugs and other drugs due to its natural material-transporting property, relatively smaller molecular structure and excellent biocompatibility, and thus has a huge potential in the field of drug carriers. For the selection of drug carriers, there are two basic principles: protection of a drug contained therein to maintain its activity in an in vivo environment; and release of the inclusion without inducing an immune response of an organism to the drug carrier. When compared to the existing drug carriers (such as an artificial liposome), the exosome has its remarkable advantages. Firstly, the exosome has its own natural inclusions, can be transferred to a receptor cell and functionally changes the receptor cells, meanwhile the surface molecules on the exosomes derived from different sources are different and have certain selectivity to the receptor cells, which is more advantageous in terms of treatment. Secondly, compared to the lower packaging efficiency of a liposome to a hydrotropic substance, which thus is limited in term of the nucleic acid delivery, while an exosome can better affiliate nucleic acid molecules and thus significantly improve the packaging efficiency. Furthermore, compared to artificially manufactured drug carriers, the exosomes derived from special cells (such as immature DC cells or mesenchymal stem cells (MSCs)) can avoid the interaction with opsin proteins, antibodies, coagulation factors, etc. due to their special surface molecules, thereby avoiding the generation of an immune response in vivo.

In view of the advantages of exosomal drugs, exosomal active formulations that inhibit endothelial cell migration are expected to open up new ideas for tumor treatment.

BRIEF SUMMARY OF THE INVENTION

The technical problem to be solved by this disclosure is to provide an exosome active formulation for inhibiting endothelial cell migration, and a preparation method and use thereof.

The technical solutions for solving the above technical problem of this disclosure are as follows: a preparation method of an exosome active formulation for inhibiting endothelial cell migration comprises the following steps:

(1) isolating primary umbilical vein endothelial cells and performing cell culture and passage;

(2) adding anisodamine to a culture medium of the subcultured endothelial cells to pretreat the endothelial cells, and then replacing the culture medium with a new endothelial cell culture medium and adding TNF-α to continue the culture of endothelial cells;

(3) extracting exosomes from the TNF-α containing endothelial cell culture medium obtained after the endothelial cells are cultivated;

(4) identifying the exosomes.

Further, the subcultured endothelial cells are endothelial cells of passages 3-5.

Further, the endothelial cell culture medium is a basic culture medium with addition of exosome-free fetal calf serum, penicillin, streptomycin and an endothelial growth factor to a final concentration of 0.05 mg/mL, 0.01 mg/mL, 0.01 mg/mL and 0.01 mg/mL, respectively.

Further, in the endothelial cell culture medium with anisodamine added in step (2), the concentration of anisodamine is $1.5 \times 10^{-2}$–$1.5 \times 10^{-3}$ ng/mL, and the time for the pre-treatment is 3-5 hours after anisodamine is added.

Further, in the endothelial cell culture medium with anisodamine added in step (2), the concentration of TNF-α is 5-15 ng/mL, and the time for culturing the endothelial cells is 18-30 hours after the TNF-α is added.

Further, the specific steps for extracting exosomes in the step (3) comprise: collecting the supernatant of the TNF-α containing endothelial cell culture medium obtained after the endothelial cells are cultivated in step (2) and centrifuging it at 4° C. and 300 g for 10 minutes, taking the supernatant and centrifuging it at 4° C. and 16,500 g for 20 minutes, taking the supernatant and filtering it via a filter membrane with a pore size of 0.2 μm, taking the filtrate and centrifuging it at 4° C. and 120,000 g for 2 hours, removing the supernatant, and dissolving the precipitates in an 0.01M PBS buffer solution.

Further, the identification of the exosomes in the step (4) comprises: observing the morphology of the exosomes with a transmission electron microscope, analyzing the particle size of the exosomes and quantifying the exosomal proteins.

Further, this disclosure provides an exosome active formulation for inhibiting endothelial cell migration prepared by the above preparation method.

The beneficial effects of this disclosure are that: the exosomes prepared by the preparation method of this disclosure can inhibit the endothelial cell migration, and the preparation method is simple.

Further, the present disclosure provides use of the exosome active formulation for inhibiting endothelial cell migration in the manufacture of antitumor drugs for inhibiting the tumor angiogenesis.

The beneficial effects of utilizing the above further solution are that: the inhibition of vascular endothelial cell migration plays an important role in the treatment of tumors, and the exosomal drugs have certain selectivity to the receptor cells and a higher delivery efficiency compared to the conventional drugs.

BRIEF DESCRIPTION OF THE SEVERAL VIEWS OF THE DRAWINGS

FIG. 1A and FIG. 1B are the transmission electron microscope diagrams of exosomes in experiment group NT10 according to this disclosure, wherein the scale in FIG. 1A is 200 nm, and the scale in FIG. 1B is 100 nm.

FIG. 2A and FIG. 2B are graph illustrations of the particle size results of exosomes detected by using a scattered light pathway of an Apogee nano flow cytometry according to this disclosure, with a gating range is 50-110 nm when detection, wherein FIG. 2A is a histogram of the detection results of standard microsphere mixtures having particle sizes of 180 nm, 240 nm, 300 nm, 590 nm, 880 nm and 1,300 nm, and FIG. 2B is a histogram of the detection result of an exosome in experiment group NT10 according to this disclosure.

FIG. 3A, FIG. 3B, FIG. 3C, FIG. 3D, FIG. 3E, and FIG. 3F are the picture illustrations showing the endothelial cell migration under the a microscope in scratch experiments of the invention, wherein FIGS. 3A, 3B, and 3C are the endothelial cells at 0 hour of the control group B, the negative control group C and the experimental group NT10, respectively; FIGS. 3D, 3E, and 3F are the endothelial cells after 13.5 hours of the control group B, the negative control group C and the experimental group NT10.

DETAILED DESCRIPTION OF THE INVENTION

Figure 4:
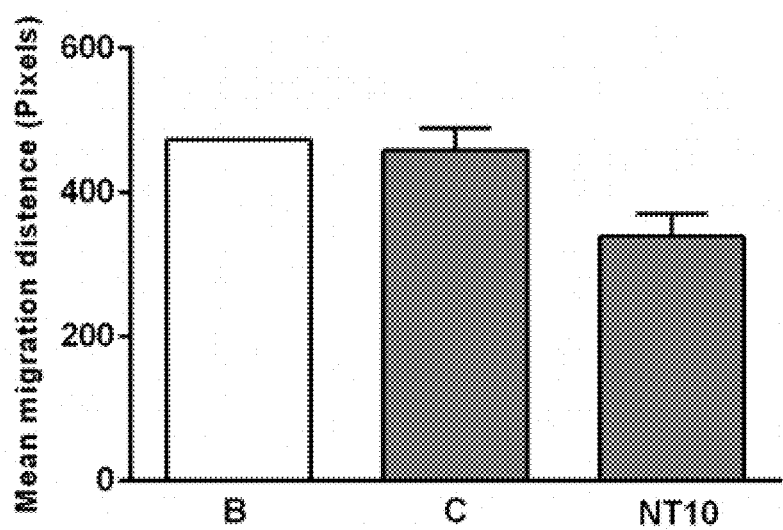
FIG. 4 is a graph illustration showing the average migration distance of cells in a single field of scratches using the Image-Pro Plus 6.0 software according to the scratch experiments of the present invention.

Hereinafter, the principle and features of this disclosure will be described in conjunction with the drawing and embodiments, and the examples are listed only for explaining this disclosure, but not for limiting the scope of this disclosure.

Example 1

Culture and Subculture of Primary Endothelial Cells

The umbilical cords of healthy delivery women were collected, and the primary umbilical vein endothelial cells were obtained by isolating via a collagenase digestion method, and primary cell culture was performed. The preparation method of an endothelial cell culture medium was as follows: an exosome-free fetal bovine serum, an endothelial growth factor, penicillin and streptomycin were added to a basic endothelial cell culture medium, wherein the final concentrations of the fetal bovine serum, the endothelial growth factor, the penicillin and the streptomycin were 0.05 mg/mL, 0.01 mg/mL, 0.01 mg/mL and 0.01 mg/mL, respectively. The devices for the cell culture were as follows: a culture flask, a culture dish and a culture plate. The conditions for the cell culture were as follows: sterile, 37° C., 5% $CO_2$, saturated humidity, and the culture medium being replaced every other day.

The primary endothelial cells were cultured for 2~3 days for passage. The digestive solution for cell passage comprised 0.25% trypsase and 0.02% EDTA. The cell culture flask was taken out, the cap was tightened, and the cell status and the confluence degree were observed under an inverted microscope. Then the subsequent operations were performed in a super-clean workbench. The old culture medium was aspirated, and a small amount of PBS was added for washing twice so as to remove serum from the residual culture medium. PBS was aspirated, and then an appropriate amount of the digestive solution was added, preferably to cover the cell monolayer. The digestive progress was observed under an inverted microscope, and the digestive solution was aspirated after the cells were retracted and rounded to be spherical shape. An appropriate amount of a complete culture medium was added to neutralize the residual digestive solution, which was evenly blown and beaten by a pipette, and the condition after digestion was observed under an inverted microscope. The cells were subcultured in separate flasks with a ratio of 1:2~1:3, and the amount of a complete culture medium was supplemented respectively, and then the caps of the culture flasks were tightened. The cells were evenly spread, and then the caps of the culture flasks were loosened with a half-turn, and subsequently the culture flasks were placed in a CO2 incubator for normal culture.

Example 2

Preparation of Exosomes

The experiments were divided into two groups, namely the experimental group NT10 and the control group C, respectively. The endothelial cells of passages 3-5 were grown to confluence in a 10 cm culture dish, wherein anisodamine with a final concentration of $1.5 \times 10^{-2}$ –$1.5 \times 10^{-3}$ ng/mL was added to the endothelial cell culture medium of the experimental group NT10 to pretreat for 4 hours, the supernatant was aspirated to remove anisodamine, and the endothelial cell culture medium was replaced by a new endothelial cell culture medium. TNF-α with a final concentration of 5 -15 ng/mL was added to continue the culture of the endothelial cells for 18-30 hours. The endothelial cells of the control group C were not pre-treated with anisodamine or treated with TNF-α.

Anisodamine used in this example was a rac-anisodamine tablet purchased from Hangzhou Minsheng Pharmaceutical Co., Ltd.

Example 3

Extraction and Purification of Exosomes

The supernatant of the TNF-α containing endothelial cell culture medium obtained after cultivation of the endothelial cells was collected and centrifuged at 300 g and 4° C. for 10 minutes. Then the supernatant was taken and centrifuged at 16,500 g and 4° C. for 20 minutes. Then the supernatant was taken and filtered by a filter membrane with a pore size of 0.2 μm. Then the filtrate was taken and centrifuged at 120,000 g and 4° C. for 2 hours. Then the supernatant was removed, and the precipitate was dissolved in 100 pL of a 0.01M PBS buffer solution to obtain an exosome active formulation for inhibiting the endothelial cell migration.

Example 4

Identification of the Exosomes

The morphology of the exosomes was observed by using a transmission electron microscope. The results were shown in FIGS. 1A and 1B, the exosomes obtained in the experimental group were globules having a homogeneous morphology with a diameter of slightly less than 100 nm and having a teacup holder-like structure with a clear membrane, which was a typical transmission electron microscope morphology of exosomes.

The particle size of the exosomes was detected by using the scattering light passageway of an Apogee nano-flow cytometry. The results were showed in FIG. 2A and FIG. 2B. FIG. 2B showed that the resultant exosomes had only one peak in the gating range of 50-110 nm, indicating that the resultant exosomes had a high purity without impurities.

The quantification of exosomal proteins was performed by using a BCA method, and the results were as shown in Table 1. The concentrations of exosomes generated in the experimental group were slightly lower than those in the control group.

TABLE 1

|  | Control group C | Experimental group NT10 |
|---|---|---|
| Detection concentration (μg/μL) | 0.145 | 0.1308 |
| Original concentration (μg/μL) | 1.451 | 1.31 |

Example 5

Influence of Exosomes from Different Sources on Migration of Human Umbilical Vein Endothelial Cells (HUVECs)

The migration of HUVECs was detected by using "a scratch method". HUVECs were cultivated in a 12-well culture plate to confluence. Straight lines were drawn with a 200 μL of pipette tip under a little force in a direction perpendicular to the surface of the cell culture, the resultant was washed with PBS twice, and the full length of the scratch traces in continuous fields was recorded under the microscope. The content of PBS in the medium was adjusted to 0.5%, and the experiments were divided into three groups, namely the blank control group B, the negative control group C, and the experimental group NT10. The experimental group NT10 and the negative control group C were interfered with exosomes respectively obtained in the NT10 group and the group C in Example 2, the blank control group was not interfered. The concentration of exosomes was adjusted to 5 μg/mL, and after cultivating under interference for 13.5 hours, the endothelial cell migration was observed. The endothelial cells in the blank control group, the negative control group and the experimental group under the microscope were shown in FIGS. 3A, 3B, 3C, 3D, 3E, and 3F, and the average migration distance of cells in a single field of scratches was measured using the Image-Pro Plus 6.0 software, and the results were shown in FIG. 4. When compared to the blank control group B without exosomes, the ability of the endothelial cell migration could be significantly inhibited by using the exosomes derived from the group NT10 of Example 2 to intervene the endothelial cells (P=0.023), and When compared to the blank control group without exosomes, the ability of the endothelial cell migration had no statistical difference by using the exosomes derived from the group C of Example 2 to intervene the endothelial cells (P =0.883). When compared to the exosomes derived from the group C of Example 2, the exosomes derived from the group NT10 of Example 2 could significantly inhibit the endothelial cell migration (P=0.006).

The experimental results according to example 5 showed that the exosomes prepared in Example 1 to Example 4 had the effect of inhibiting the endothelial cell migration, and could be used in the manufacture of anti-tumor drugs for inhibiting the tumor angiogenesis.

The above descriptions are preferred examples of this disclosure, but are not for limiting this disclosure. All of the changes, equivalents, modifications, and the like made within the spirit and principle of this disclosure are included in the protection scope of this disclosure.

We claim:
1. A method of preparing an exosome active formulation capable of inhibiting endothelial cell migration comprising:
   (a) isolating primary umbilical vein endothelial cells
   (b) culturing and passaging the primary umbilical vein endothelial cells in a first culture medium, thereby forming a culture comprising subcultured endothelial cells in a first medium;
   (c) adding $1.5 \times 10^{-3}$-$1.5 \times 10^{-2}$ ng/mL anisodamine to the first medium to pretreat the subcultured endothelial cells;
   (d) 3-5 hours after adding the anisodamime, replacing the first medium with a new endothelial cell culture medium;
   (e) adding 5-15 ng/mL TNF-α to the new endothelial cells culture medium;
   (f) culturing the cells in the new endothelial cell culture medium with TNF-α for 18-30 hours after adding the TNF-α, thereby forming a culture comprising cultivated endothelial cells in a second medium;
   (g) extracting exosomes from the second medium; and
   (h) identifying the exosomes.
2. The method of claim 1, wherein step (b) comprises passaging the primary umbilical vein endothelial cells 3-5 times to form the subcultured endothelial cells.

3. The method of to claim 1, wherein the new endothelial cell culture medium is a basic culture medium plus 0.05 mg/mL exosome-free fetal calf serum, 0.01 mg/mL penicillin, 0.01 mg/mL streptomycin and 0.01 mg/mL endothelial growth factor.

4. The method of claim 1, wherein the step (g) comprises:
   (i) collecting a supernatant of the second medium;
   (ii) centrifuging the supernatant of step (i) at 4° C. and 300 g for 10 minutes;
   (iii) centrifuging the supernatant of step (ii) at 4° C. and 16,500 g for 20 minutes;
   (iv) filtering the supernatant of step (iii) through a filter membrane having a pore size of 0.2 µm;
   (v) centrifuging the filtrate of step (iv) at 4° C. and 120,000 g for 2 hours;
   (vi) removing the supernatant of step (v); and
   (vii) dissolving the solids of step (v) in a 0.01 M PBS buffer solution.

5. The method of claim 1, wherein the step (h) comprises:
   observing the morphology of the exosomes with a transmission electron microscope;
   analyzing the particle size of the exosomes; and
   quantifying the exosomal proteins.

6. An exosome active formulation for inhibiting endothelial cell migration produced by the method of claim 1.

* * * * *